United States Patent [19]
Hell et al.

[11] Patent Number: 5,761,268
[45] Date of Patent: Jun. 2, 1998

[54] X-RAY DIAGNOSTIC APPARATUS

[75] Inventors: Erich Hell, Erlangen; Gustav-Adolf Voss, Hamburg, both of Germany

[73] Assignee: Siemens Aktiengesellschaft, Munich, Germany

[21] Appl. No.: 811,287

[22] Filed: Mar. 4, 1997

[30] Foreign Application Priority Data

Mar. 5, 1996 [DE] Germany .................. 196 08 497.0

[51] Int. Cl.[6] .................................................. H01J 35/30
[52] U.S. Cl. .......................................... 378/137; 378/113
[58] Field of Search ................................ 378/113, 137, 378/138

[56] References Cited

U.S. PATENT DOCUMENTS 4,075,489  2/1978  Neal et al. ................... 378/113 X
4,631,741  12/1986  Rand et al. .................. 378/113 X
5,224,137  6/1993  Plomgren et al. .
5,491,734  2/1996  Boyd et al. .

OTHER PUBLICATIONS

"Introduction To X-Ray Spectrometric Analysis," Bertin, pp. 8-11, 22-49. No date.

*Primary Examiner*—David P. Porta
*Attorney, Agent, or Firm*—Hill & Simpson

[57] ABSTRACT

In an X-ray diagnostic apparatus, for acquiring the cross-section, position and/or alignment, relative to a target, of an electron beam generated by an electron generating system, at least one conductor is provided in the region of the target so that a signal can be derived by the conductor under the influence of the electron beam and supplied to an evaluation stage. The conductor is composed of a material having an atomic number lower than that of tungsten, so that no undesirable radiation arises due to the interaction of the electrons with this conductor.

9 Claims, 2 Drawing Sheets

5,761,268

X-RAY DIAGNOSTIC APPARATUS

BACKGROUND OF THE INVENTION

1. Field of the Invention

The present invention is directed to an X-ray diagnostic apparatus of the type wherein the cross-section, position and/or alignment of the electron bundle relative to a target is monitored, the electron bundle being incident on the target for producing X-rays.

2. Description of the Prior Art

It is known to provide an X-ray diagnostic apparatus with an electron generating device, means for focussing the electrons into a bundle and for accelerating the electrons onto a target for generating X-radiation, deflection means for deflecting the electrons along the target, and a device for detecting the cross-section, the position and/or the alignment of the electron bundle relative to the target, this device having at least one conductor in the region of the target such that a signal can be derived under the influence of the electron bundle. In such an X-ray diagnostics apparatus known from U.S. Pat. No. 5,224,137, the conductor is manufactured of a tungsten wire. A signal supplied to an evaluation means can be derived at the tungsten wire under the influence of the electron bundle. The evaluation means generates an output signal for setting the cross-section, the position and/or the alignment of the electron bundle relative to the target.

SUMMARY OF THE INVENTION

The present invention is based on the perception that in known system of the type described above, radiation, particularly X-radiation, could be generated by electrons striking the tungsten wire, having a disadvantageous effect on the image generation.

It is therefore an object of the invention to provide an X-ray diagnostic apparatus of the type initially described wherein this undesirable X-radiation does not occur, or only occurs to as small an extent as possible.

The above object is achieved in accordance with the principles of the present invention in an X-ray diagnostic apparatus of the type generally described above wherein the conductor which is used to generate a signal from which the cross-section, position and/or alignment of the electron beam relative to the target is identified, is composed of a material having an atomic number which is lower than the atomic number of tungsten.

An advantage of the invention is that, by the use of a conductor composed of a material with an atomic number lower than that of tungsten and, in particular, a conductor executed as a carbon filament, no disturbing radiation, particularly X-radiation, is produced by the apparatus.

DESCRIPTION OF THE PREFERRED EMBODIMENTS

Figure 1:
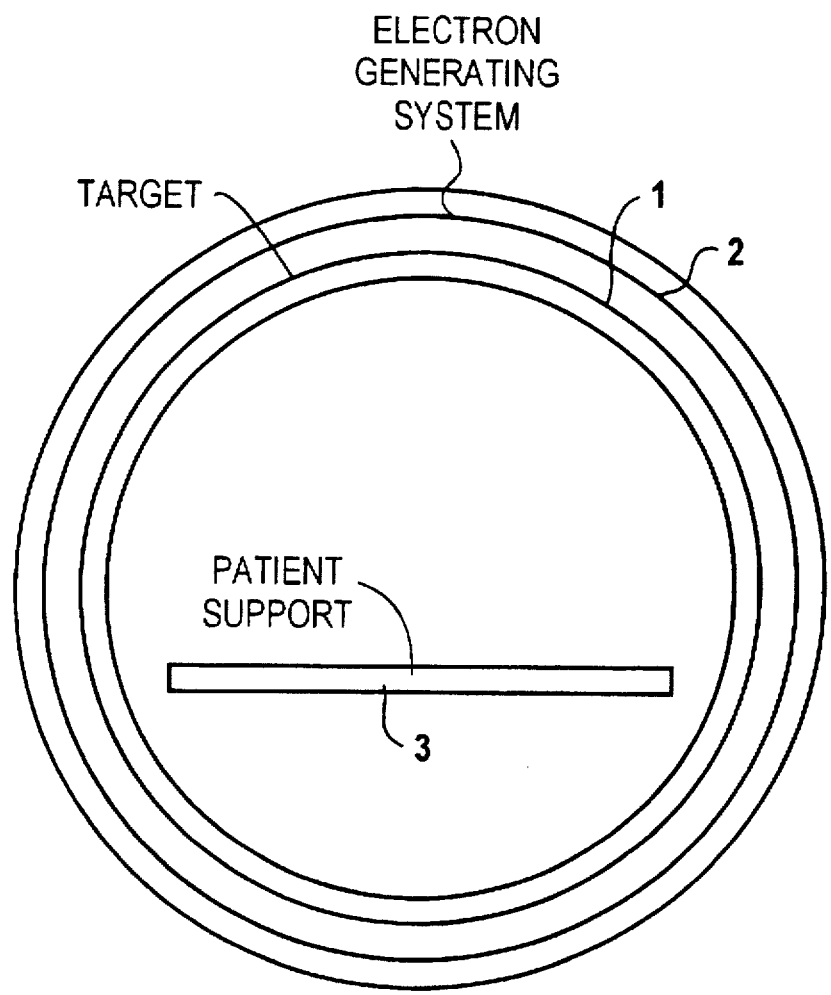
FIG. 1 is a schematic illustration of an X-ray diagnostics apparatus in the form of a computed tomography apparatus in which the invention can be utilized.

FIG. 1 schematically shows an X-ray diagnostic apparatus implemented as a computed tomography apparatus having an annular, evacuated arrangement in which a target 1, an electron generating system 2 and means (yet to be described in greater detail) for focussing the electrons into a beam and for accelerating the electrons onto the target 1 for generating X-radiation. The ring arrangement surrounds a support 3 for an examination subject. By deflecting the electron beam along the target 1, thus, a X-ray beam that scans the examination subject and that is acquired by a detector means (not shown) can be generated. Dependent on the radiation shadow of the examination subject, the detector means generates signals that are supplied to an evaluation means for generating an image on a display means.

Figure 2:
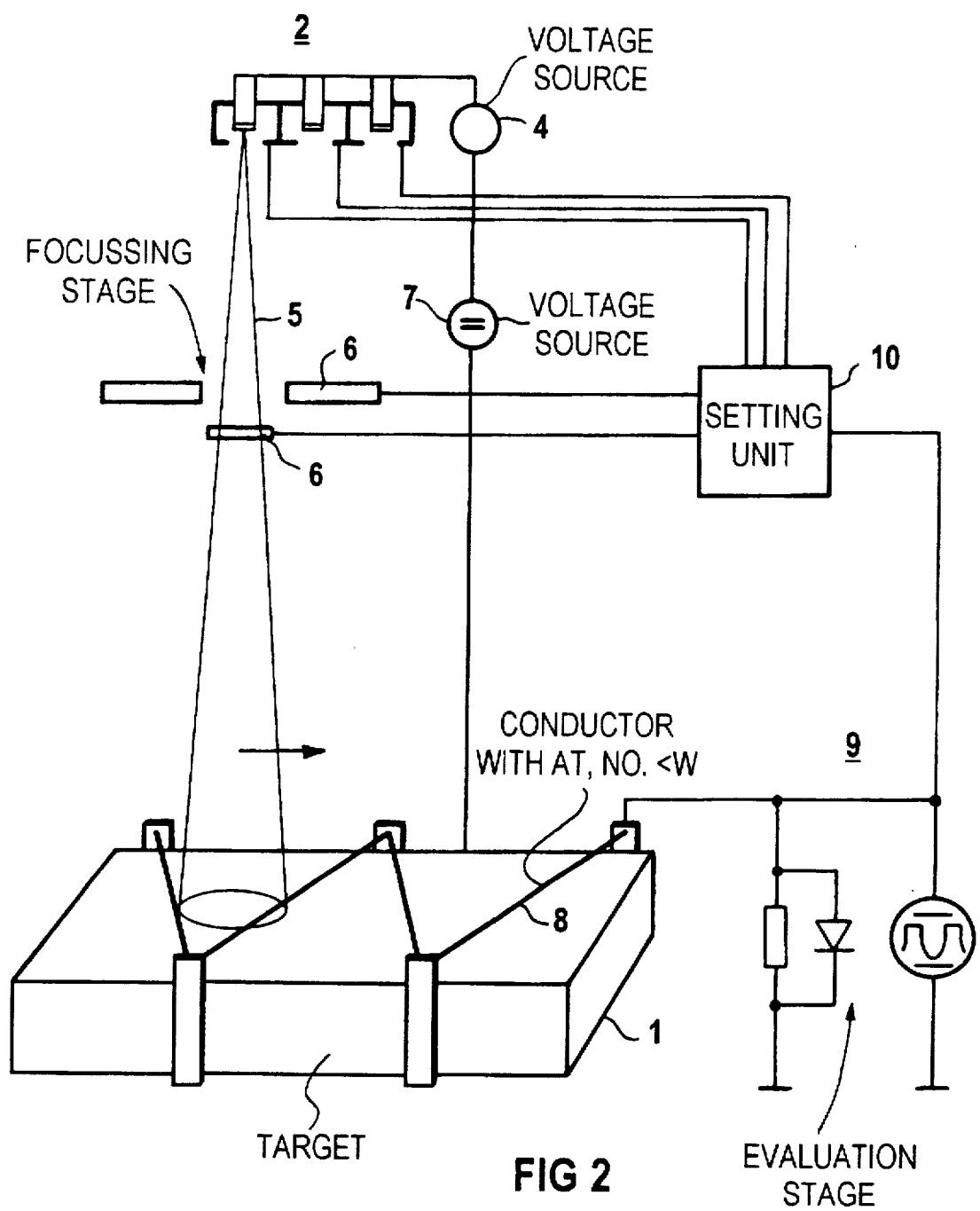
FIG. 2 is a detailed illustration of the X-ray diagnostics apparatus of the invention.

Parts of the X-ray diagnostics apparatus that are important for the invention are shown in more detail in FIG. 2. For example, the electron generating device 2 can be composed of individual thermionic cathodes joined to one another that can be excited to emit electrons by an allocated, controllable voltage source 4. It is alternatively possible to use only a single electron generating means according to U.S. Pat. No. 5,224,137. The electron generating system 2 generates an electron beam 5 that is deflected along the target 1 a suitable, known deflection means. It is also possible to provide an electron generating means such that an electron beam is generated that is supplied into the ring arrangement in the radial direction and is guided parallel to the target 1 via a guide magnetic field, and is deflected onto the target 1 by a kick magnetic field that is preferably controllable for generating X-radiation.

FIG. 2 schematically shows a focussing stage 6 for focussing the electrons to a beam. This focussing stage 6 can include either electrodes or magnets that are arranged in pairs offset by 90° relative to one another and that can be supplied with a voltage. A voltage of a second voltage source 7 is applied between the target 1 and the electron generating system 2, so that the electrons emanating from the electron generating system 2 are accelerated onto the target 1 for generating X-radiation. An arrangement for detecting the cross-section, the position and/or the alignment of the electron beam 5 is disposed in the region of the target 1. In accordance with the invention, this arrangement has at least one conductor 8 that is composed of a material with an atomic number lower than that of tungsten. In the exemplary embodiment, this conductor is stretched zig-zag-like along the target 1 and is preferably a carbon filament. An evaluation stage 9 that generates an output signal dependent on the cross-section, the position and/or the alignment of the electron beam 5 is connected to this conductor 8. Under the influence of the electron beam 5, a signal can be derived at the conductor 8 that is evaluated by the evaluation stage 9. On the basis of the output signal of the evaluation stage 9, the focussing stage 6 and/or the deflection means is influenced by a setting unit 10 so that the cross-section, the position and/or the alignment of the electron beam 5 meets predetermined criteria.

Within the scope of the invention, the conductor 8 can be a sole conductor that, as shown, is stretched zig-zag-like along the target 1, however, it is also possible to provide a number of individual conductors 8 whose respective signals can be supplied to the evaluation stage 9. This invention is not limited to employment in a computed tomography apparatus, but can be used everywhere where an electron beam is to be monitored in view of its cross-section, position and/or alignment. The target can not only be arcuately fashioned, as shown in the exemplary embodiment, but also can extend along a straight line in other types of X-ray diagnostic apparatuses.

The carbon filament can have a thickness in a range from 5 to 50 µm, preferably approximately 10 µm, and is positioned electrically insulated at a slight distance above the target 1. The alignment of the conductor 8 with reference to the target 1 is to be selected such that the electron beam distribution can be measured on-line directly in front of the target 1 both in the azimuthal and radial directions.

Although modifications and changes may be suggested by those skilled in the art, it is the intention of the inventors to embody within the patent warranted hereon all changes and modifications as reasonably and properly come within the scope of their contribution to the art.

We claim as our invention:

1. An X-ray diagnostic apparatus comprising:

means for generating electrons;

a target;

means for focussing said electrons into an electron beam and for accelerating the electrons in said electron beam onto said target for generating X-rays;

deflection means for deflecting the electrons in said electron beam along said target;

at least one conductor disposed in a region of said target and interacting with said electron beam for generating a signal dependent on an influence of said electron beam on said conductor, said conductor being composed of a material having an atomic number which is less than the atomic number of tungsten; and evaluation means, supplied with said signal, for identifying at least one of a cross-section of said electron beam, a position of said electron beam and an alignment of said electron beam relative to said target.

2. An X-ray diagnostic apparatus as claimed in claim 1 wherein said conductor comprises a carbon filament.

3. An X-ray diagnostic apparatus as claimed in claim 1 comprising a plurality of conductors disposed in said region of said target.

4. An X-ray diagnostic apparatus as claimed in claim 1 wherein said evaluation means comprises means for generating an output signal corresponding to at least one of said cross-section, position and alignment of said electron beam.

5. An X-ray diagnostic apparatus as claimed in claim 4 further comprising setting means, supplied with said output signal from said evaluation means, for acting on at least one of said means for focussing and said deflection means for causing said at least one of said cross-section, said position and said alignment of said electron beam to meet predetermined criteria.

6. An X-ray diagnostic apparatus as claimed in claim 1 comprising means for mounting said conductor to follow a substantially zig-zag path along said target.

7. An X-ray diagnostic apparatus as claimed in claim 1 wherein said target comprises an arcuate target.

8. An X-ray diagnostic apparatus as claimed in claim 1 wherein said target comprises a target in a computed tomography apparatus.

9. An X-ray diagnostic apparatus as claimed in claim 1 wherein said target extends along a straight line.

* * * * *